United States Patent [19]
Chow

[11] Patent Number: 5,016,633
[45] Date of Patent: May 21, 1991

[54] ARTIFICIAL RETINA DEVICE

[76] Inventor: Alan Y. Chow, 191 Palamino Pl., Wheaton, Ill. 60187

[21] Appl. No.: 390,562

[22] Filed: Aug. 8, 1989

[51] Int. Cl.$^5$ .......................... A61N 1/00; A61F 2/14
[52] U.S. Cl. .............................. 128/419 R; 128/784; 623/4
[58] Field of Search ......... 623/4; 128/419 R, 783–785

[56] References Cited

U.S. PATENT DOCUMENTS

| | | | |
|---|---|---|---|
| 2,760,483 | 10/1954 | Tassicker | 623/4 X |
| 3,594,823 | 7/1971 | Collins | 623/66 X |
| 3,628,193 | 12/1971 | Collins | 128/419 R |
| 3,766,311 | 10/1973 | Boll | 623/66 X |
| 3,848,608 | 11/1974 | Leonard | 128/419 R |
| 3,914,800 | 10/1975 | Collins | 623/66 X |
| 4,272,910 | 6/1981 | Danz | 623/4 X |
| 4,551,149 | 11/1985 | Sciarra | 623/4 |
| 4,601,545 | 7/1986 | Kern | 623/4 X |
| 4,628,933 | 12/1986 | Michelson | 128/419 R |

OTHER PUBLICATIONS

Science News, Feb. 2, 1974, vol. 105, No. 5, p. 105.
Science, Jul., 1981.

*Primary Examiner*—Ronald Frinks
*Attorney, Agent, or Firm*—Willian Brinks Olds Hofer Gilson & Lione

[57] ABSTRACT

A silicon chip device composed of a large array of densely packed microphotodiodes is implanted between the inner and outer retina layers, in patients with vision-deficient eyes suffering from retinal dysfunction, to allow for useful formed vision. The photoactive surface of each photodiode, with its silicon deposited or etched electrode, point towards the incident light. The device produces an amplitude-modulated current to stimulate the inner retinal layer. The device is intrinsically inert due to its doped silicon substrate nature.

15 Claims, 7 Drawing Sheets

ARTIFICIAL RETINA DEVICE

BACKGROUND OF THE INVENTION

The present invention is directed to a medical product and operation procedure which can be used to correct vision loss or even complete blindness caused by certain retinal diseases. A variety of retinal diseases, for example, cause vision loss or blindness by destruction of the choroid, choriocapillaris, and the outer retinal layers. The outer layers include Bruch's membrane and retinal pigment epithelium, the loss of which results in degeneration of the inner retinal photoreceptor layer. These diseases, however, often spare much of the remaining inner retinal layers of the outer nuclear, outer plexiform, inner nuclear, inner plexiform, ganglion cell and nerve fiber layers.

The current invention involves the use of an electronic device, a photosensitive array, that is capable of mimicking the signals that would otherwise be produced by the damaged inner retinal photoreceptor layer. When the device is implanted between the inner and outer retinal layers, it will stimulate the inner layer to provide significantly useful formed vision to a patient in a manner never before available.

Prior attempts have been made to produce vision by stimulating various portions of the retina. One such attempt involved an externally powered but internally located photosensitive array device with its photoactive surface and electrode surface on opposite sides. The device was to stimulate the nerve fiber layer via direct placement on this layer from the vitreous body side. The success of this device is unlikely due to it having to duplicate the complex frequency modulate neural signals of the nerve fiber layer. Furthermore, the nerve fiber layer runs in a general radial course with many layers of overlapping fibers from different portions of the retina making selection of the appropriate nerve fiber to stimulate extremely difficult if not impossible. The production of useful formed visual imagery is therefore highly unlikely. No device of this type has been known to have been constructed that produced any type of formed image.

Another prior device involved a unit consisting of a supporting base onto which a photo-sensitive material such as selenium is coated. This device was to have been inserted through an external scleral incision made at the posterior pole resting between the sclera and choroid or between the choroid and retina. Light simulation would then cause a potential to develop on the photosensitive surface causing ions to be produced which would then theoretically migrate into the retina causing stimulation. However, having no discrete surface structure to restrict the directional flow of charges, lateral migration and diffusion of charges would be allowed thereby preventing any resolution capability. Placement of this device between the sclera and choroid would also virtually block the discrete migration of ions to the photoreceptor and inner retinal layers due to the presence of the choroid, choriocapillaris, Bruch's membrane and the retinal pigment epithelial layer. Placement of the device between the choroid and the retina would still interpose Bruch's membrane and the retinal pigment epithelial layer in the pathway of discrete ion migration. Also, as this device would have had to be inserted into or through the highly vascular choroid of the posterior pole, severe subchoroidal, intraretinal and or intraorbital hemorrhage would likely have resulted along with disruption of blood flow to the posterior pole. One such device was apparently constructed and implanted into a patient's eye resulting in reported light perception but no formed imagery.

SUMMARY OF THE INVENTION

The artificial retina device of this invention circumvents the limitations of previous devices. It is composed of a plurality of discrete photodiodes with their individual electrodes disposed on one surface of a substrate, the photodiodes each being connected to a common electrical ground on the other side of the substrate. Each photodiode includes an active electrode layer overlaying a photosensitive layer, and each is connected to an electrical ground. The photodiodes have electrical outputs that correspond to the amplitude of the light incident on said device, whereby said device can be implanted in the eye intermediate the inner retinal layer and the retinal pigment epithelium of outer layer of the retina, so that each of said photodiodes will stimulate directly individual or small groups of cells in the inner retinal layer corresponding to the light incident on said device.

When inserted within the retina between the inner and outer retinal layers, in the potential space zone, an amplitude-modulated electric potential, varying with illumination, produced by each photodiode will stimulate the overlying inner retinal layer consisting of photoreceptors, bipolar cells and horizontal cells. As these cells normally both receive and produce analog amplitude-modulated currents, the analog amplitude-modulated output of the device is well suited for stimulation of these cells. The amplitude-modulated signals of the bipolar cells are then modified and converted by the amacrine and ganglion cells to a frequency-modulated signal as is the normal biological event in the innermost area of the inner retinal layer for distant transmission through the optic nerve to the lateral geniculate area of the brain. Because the complex conversion of the amplitude-modulated signal to the frequency-modulated signal is left to intrinsic retinal mechanisms, the formed vision produced is much enhanced compared to devices that attempt to stimulate the nerve fiber layer directly with electronic and amplifier reconstructed frequency-modulated signals.

DETAILED DESCRIPTION OF THE PRESENTLY PREFERRED EMBODIMENTS

Figure 1A:
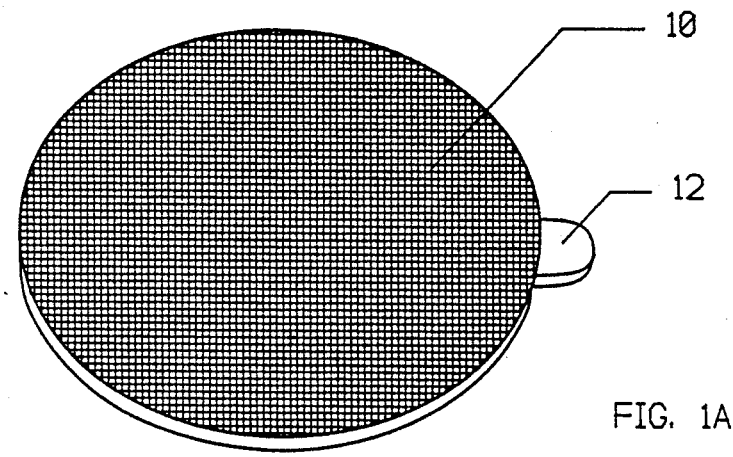
FIG. 1A is a perspective view of an artificial retina device of the present invention.
Figure 1B:
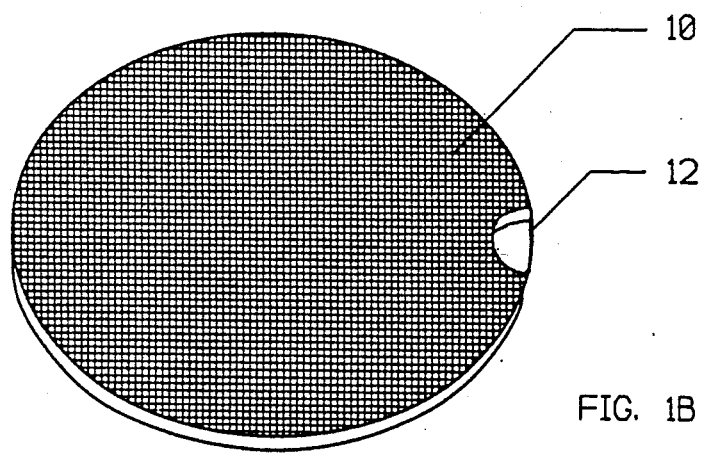
FIG. 1B is a perspective view of an alternative form of an artificial retina device of the present invention.

In one embodiment of this invention, an artificial retina device 10 is generally circular in shape with an integral grasping member (FIG. 1B) or a projecting grasping member (FIG. 1A) to grasp the device while it is being inserted. The device ranges from 3 mm to 20 mm in diameter and from 0.005 mm to 2 mm in thickness.

Figure 1C:
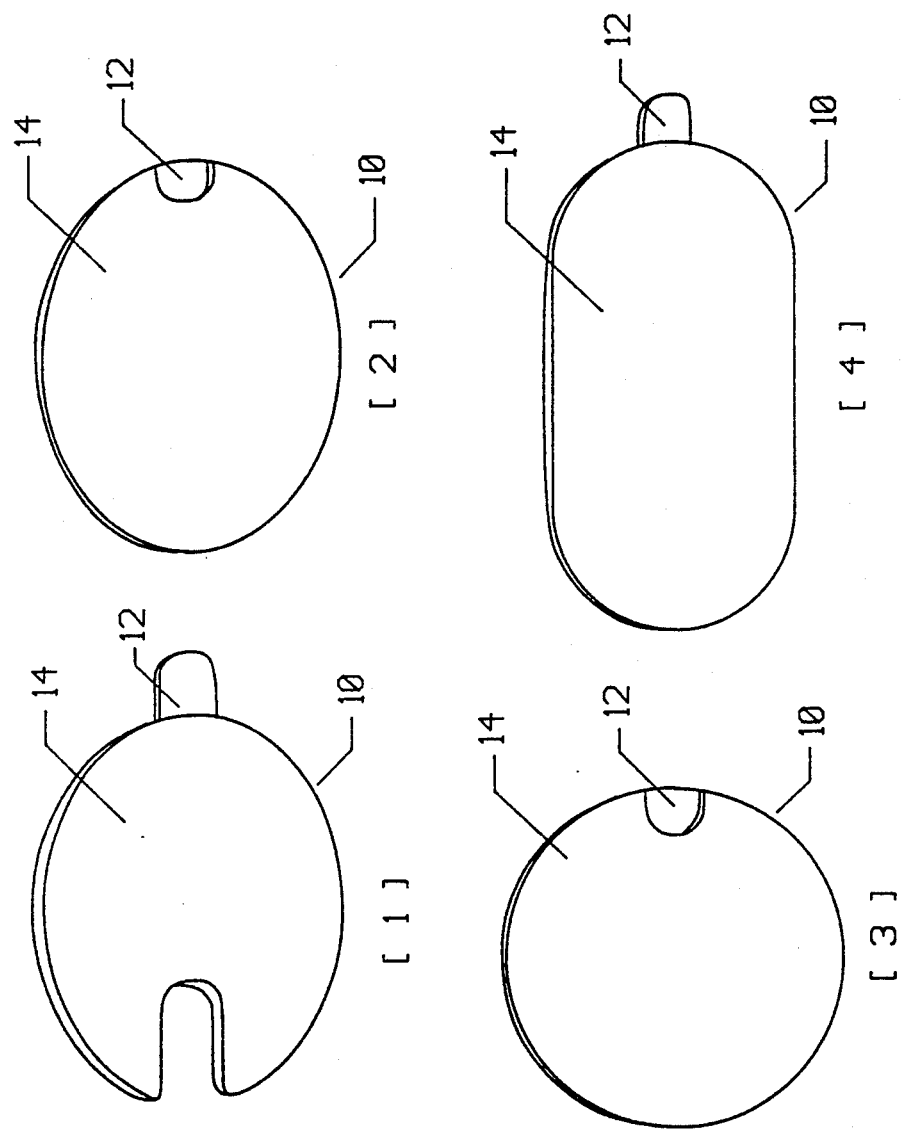
FIG. 1C (1)–(4) are perspective views of four alternative embodiments of the present invention.

As shown in FIG. 1C, the device 10 may be round (FIG. 1C (3)), oval (FIG. 1C (4)) elliptical (FIG. 1C (2)), or irregular (FIG. 1C (1)) in shape. The surface contours may be flat or curved to match the curvature of the retina. The edges or selected areas of the anterior 14 or posterior 16 (FIG. 2A) surfaces may be fashioned with ridges or other protrusions to improve stability within the retina and to improve biological acceptability. The device may also have ledges, lips or loops to aid manipulation during implantation. In addition, it may also have openings (not shown) between the two surfaces to allow passage of intraretinal nourishment and tissue ingrowth to maintain the device securely in the retina.

Figure 2A:
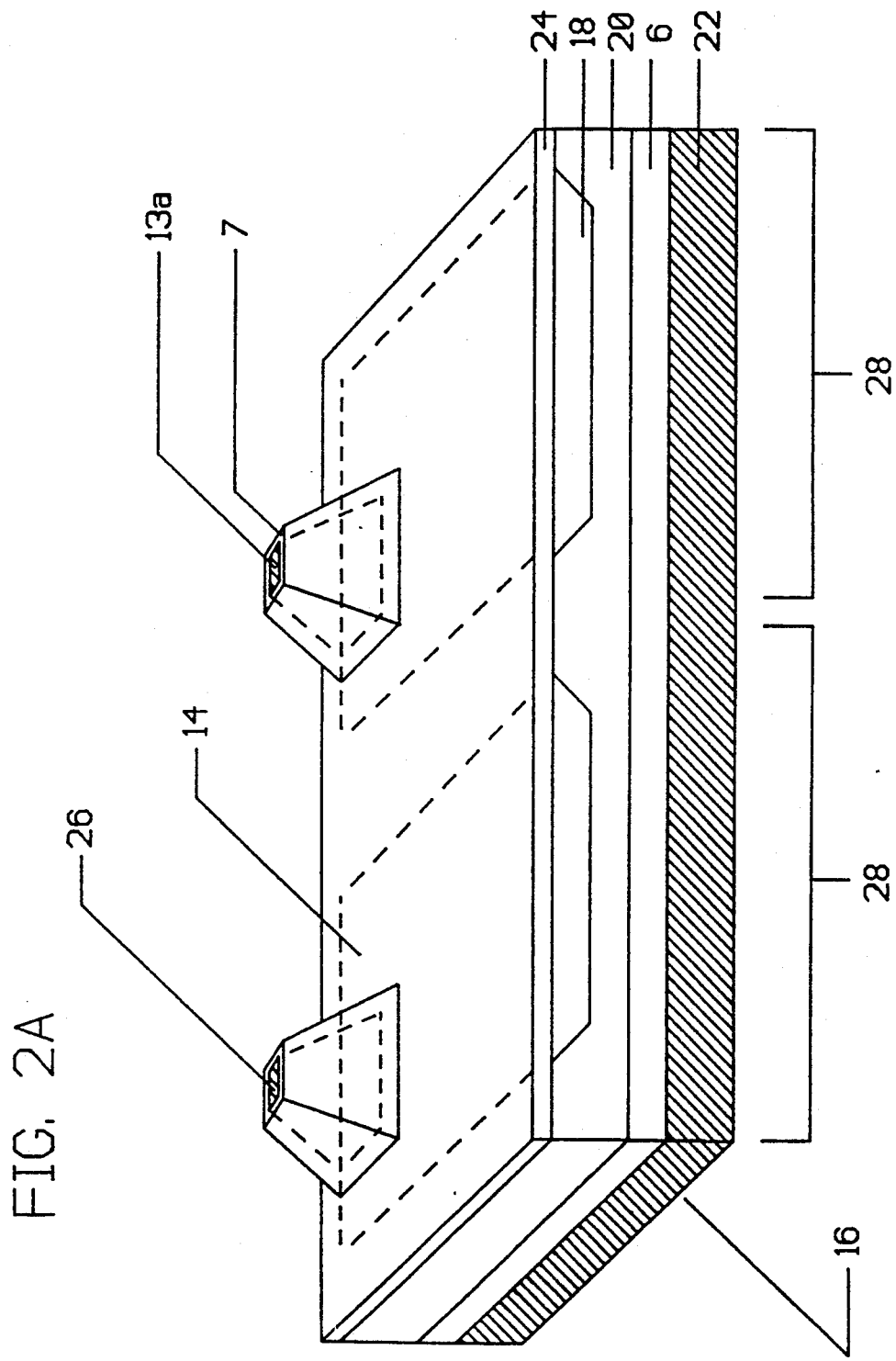
FIG. 2A is a perspective, cross-sectional view of a first photodiode array for use in an artificial retina device of the present invention.
Figure 2B:
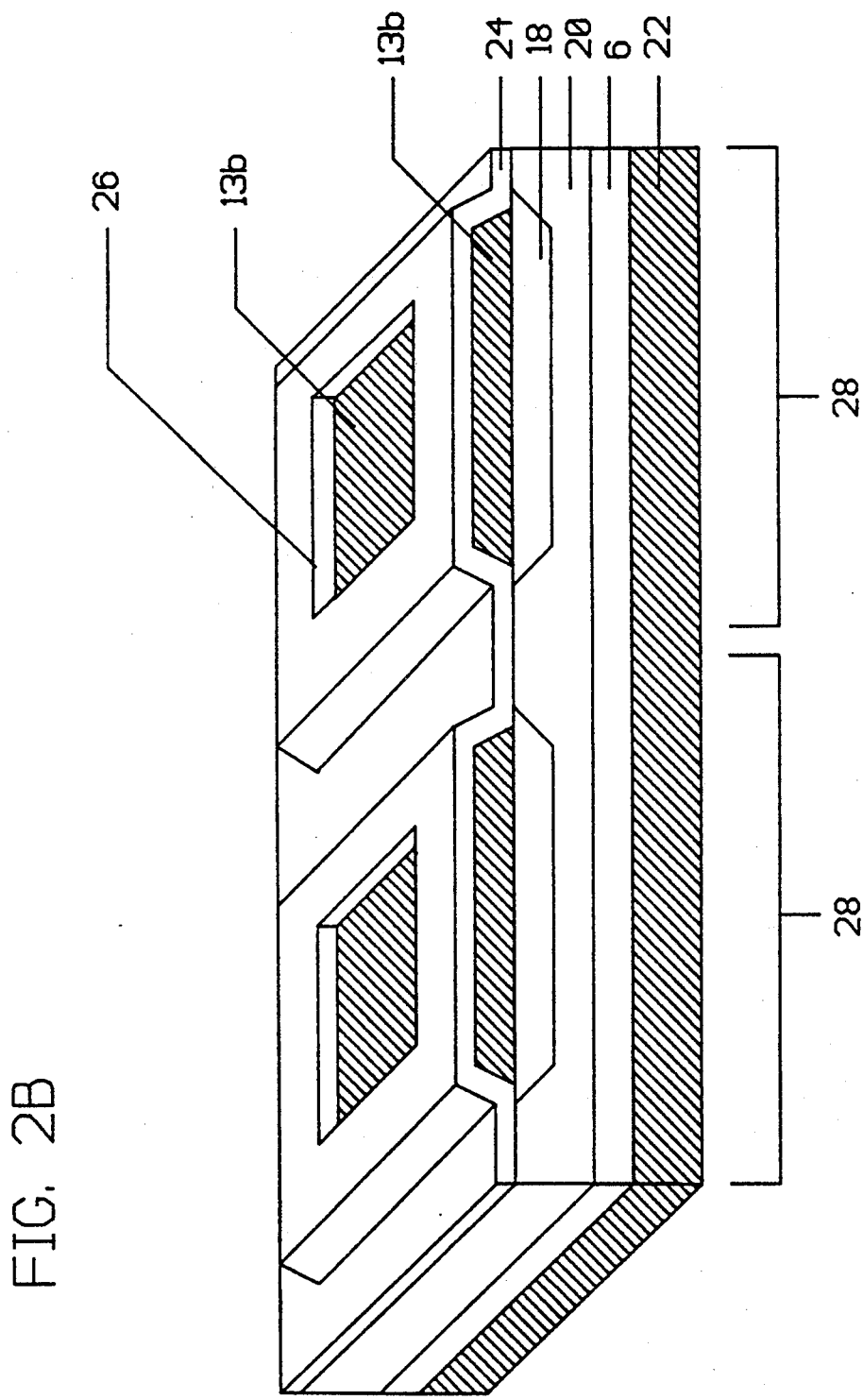
FIG. 2B is a perspective, cross-sectional view of a second photodiode array for use in an artificial retina device of the present invention.

As shown in FIGS. 2A and 2B, the details of the photodiode construction of the artificial retina device of the present invention consist of multiple layers of both pure and doped silicon deposited and etched. An insulated or noninsulated polysilicon active electrode structure 13a projects from the surface in one embodiment (FIG. 2A), or a flat polysilicon active electrode surface 13b is constructed in another alternative embodiment (FIG. 2B) to transfer a current from the photodiode to the overlying photoreceptor, bipolar and inner retinal cell layers as explained in detail below. In particular, the polysilicon electrode structure 13a or 13b can be made by standard semiconductor plasma and/or wet etch techniques.

The artificial retina device of the present invention is, therefore, a large array of photovoltaic microphotodiodes of the PiN type. Each microphotodiode consists of a shallow P-doped photoactive layer 18 overlaying an intrinsic layer 20 which in turn overlays a N-doped layer 6. On the posterior surface of layer 6 is deposited a conductive layer 22 of polysilicon that forms the common complimentary electrode or ground. A common complimentary electrode is shown, but the device can be constructed with a discrete complimentary electrode for each microphotodiode.

On the anterior surface is deposited a layer of silicon nitrate 24 covering the entire surface except for openings (or on the unmasked areas) 26 that establish electrode contact areas for the polysilicon active electrode 13a (or 13b). The PiN layers may be reversed (NIP) or modified to facilitate reversal of the device polarity. As can be seen in FIGS. 2A and 2B, a plurality of nodes 28 are formed from a plurality of microphotodiodes described above. The designed current output of each self-powered photodiode node is on the order of 50 nA when the device is exposed to average room lighting. However, the electrical current output may be designed to be greater or less than this value depending upon the stimulation requirement of the overlying cell layer. A supplemental bias activation current may also be provided by an insulated wire or series of insulated wires leading from the device from the eye into an external or internally implanted battery unit.

Figure 3A:
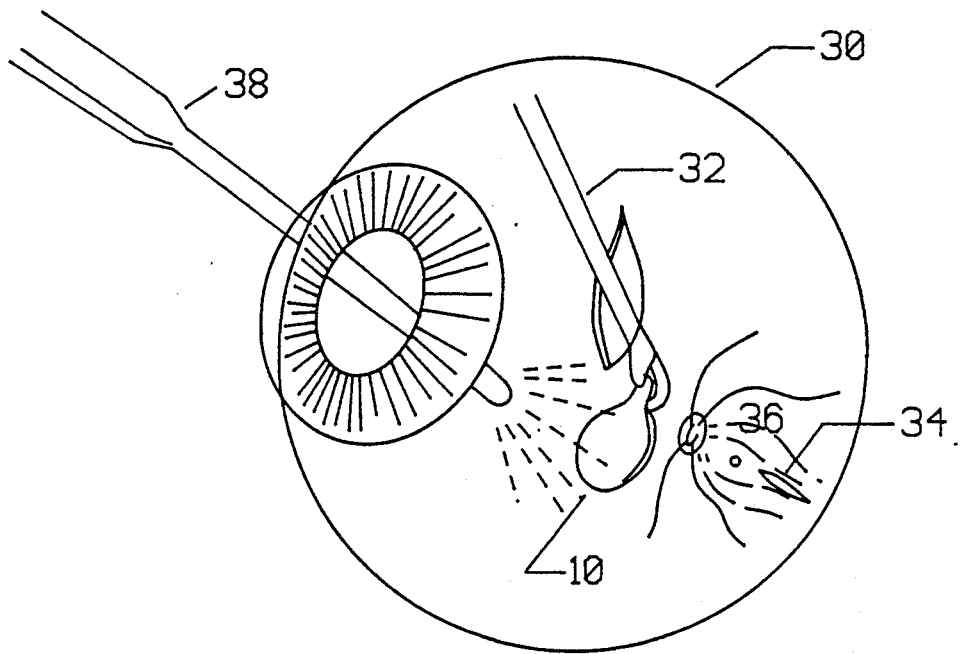
FIG. 3A–3C illustrate steps in a surgical procedure for implanting an artificial retina device of the present invention.
Figure 3B:
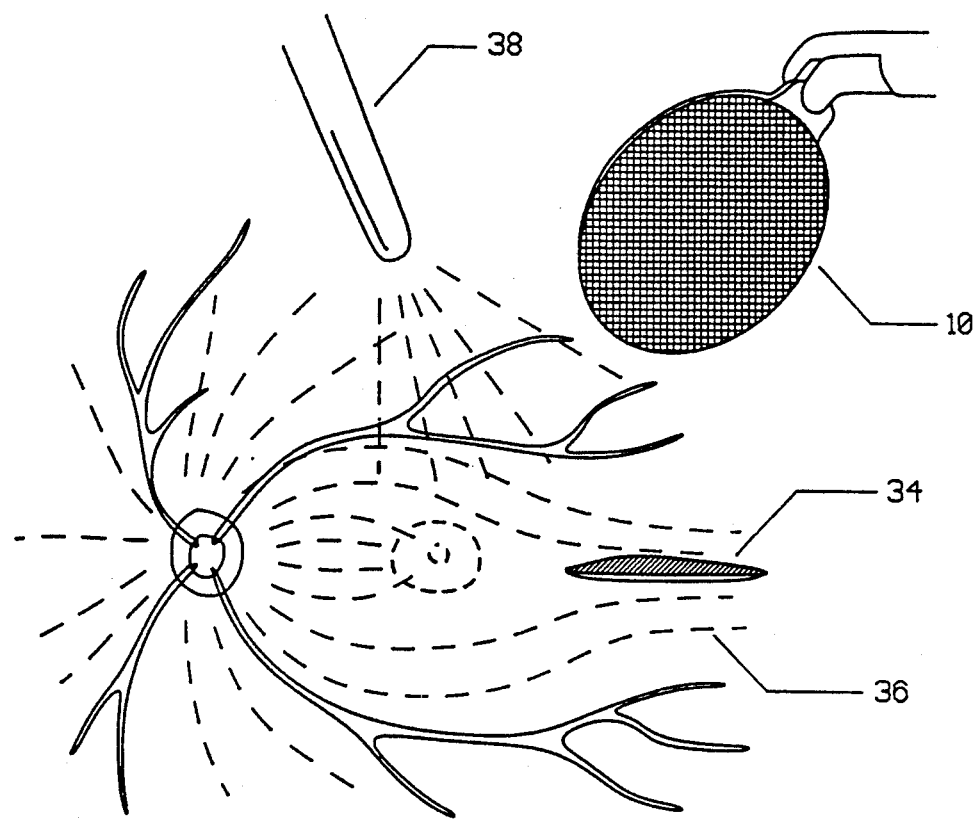

As shown in FIG. 3A, the device 10 of this invention is inserted into the vitreous cavity of the eye 30 via a pars plana incision 32. A horizontal incision 34 (FIG. 3B) is then made through the retina from the vitreous side in the temporal portion of the posterior pole into the potential space between the photoreceptor layer and the retinal pigment epithelium. A horizontal incision 34 made at this location will avoid cutting inner retinal vasculature and will be parallel to coursing nerve fiber layers 36, therefore, also avoiding their injury. Illumination for the surgical procedure is provided by a optical fiber light pipe 38. The potential space is then be opened by canula irrigation of a balanced salt solution into the intraretinal space.

Figure 3C:
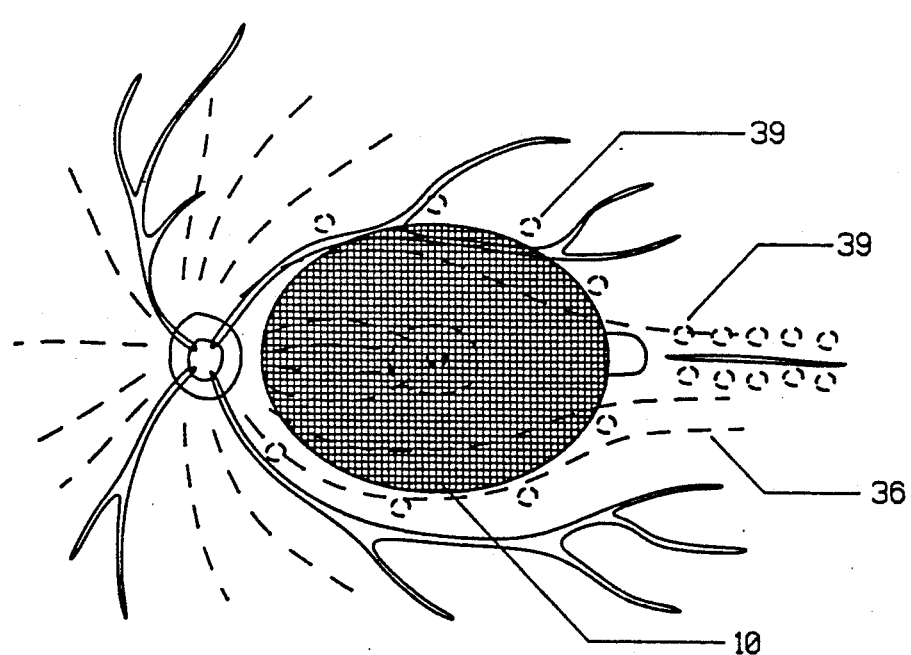

The device is then placed into the intraretinal cavity (FIG. 3C) at the posterior pole under the macula area. Specifically, the device is placed between the retinal pigment epithelium 58 (FIG. 4) and photoreceptor layer 54, or if photoreceptor layer 54 is atrophied or lost then between the retinal pigment epithelium 58 and the bipolar and horizontal cell layer 52. The device is positioned such that the electrical ground 22 is overlaying the retinal pigment epithelium 58 and the active electrode 13a (or 13b) faces the incident light.

After insertion, a series of endolaserphtocoagulation or endocautery burns 39 are made around the periphery of the device to secure the device. The scar tissue so formed around the periphery of the device will prevent the device from moving out of position. Endolaserphotocoagulation or endocautery 39 may also be used to seal the retinal incision. Air or other approved gaseous compounds may also be injected into the vitreous cavity to tamponade the retinal opening during healing. The pars plana incision will be closed in the usual surgical manner.

An alternate method for implantation would involve making an incision through the sclera just posterior to the ora serata. Dissection would proceed through the choroid, choriocapillaris, Bruch's membrane and retinal pigment epithelium under stereo operating microscrope control into the potential space between the inner and outer retinal layers. The artificial retinal implant would then be inserted into this space and directed posteriorly towards the macula by a pushing action imparted by a formed curved iris spatula. The device will rest in the macula area of posterior pole of the eye between the inner and outer retinal layers.

Figure 4:
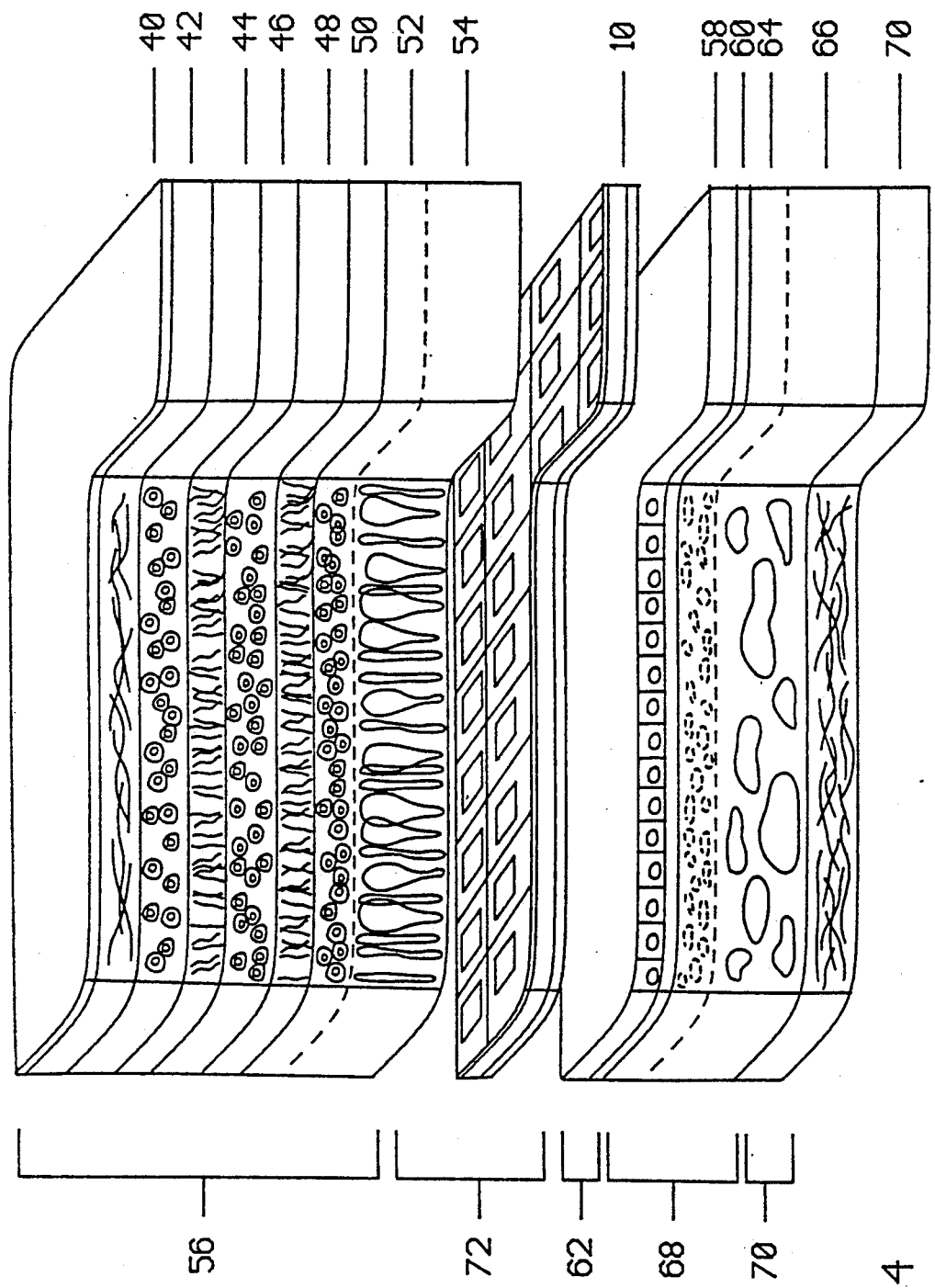
FIG. 4 is an exploded, cross-sectional view of an artificial retinal device of the present invention as implanted in the eye.

The layers of the eye at the posterior pole from inside to outside are shown in FIG. 4: internal limiting membrane 40, nerve fiber layer 42, ganglion and amacrine cell layer 44, inner plexiform 46, inner nuclear layer 48, outer plexiform 50, outer nuclear and bipolar cell layer 52, and photoreceptor layer 54, all of which constitute the inner retinal layer 56. The retinal pigment epithelium 58, and Bruch's membrane 60 constitute the outer retinal layer 62. The choriocapillaris 64, and choroid 66 comprise the choroidal vasculature 68. The outer coat of the eye is the sclera 70.

With regard to FIG. 4, when the device 10 is inserted within the retina between the inner retinal layer 56 (that may or may not contain a functional photoreceptor layer 54) and the outer retinal layer 62, in the potential space zone 72, an amplitude-modulated current varying with illumination, produced by each photodiode of the device 10 will stimulate the overlying inner retinal layer consisting of photoreceptors (if present) and their cell bodies 54, 52, bipolar cells 48 and horizontal cells 52. As cells 48–52 normally both receive and produce analog amplitude-modulated currents, the analog amplitude-modulated output of the device is well suited for stimulation of these cells. The amplitude-modulated signals of the bipolar cells 48 are then modified and converted by the amacrine and ganglion cells 44 to a frequency-modulated signal as is the normal biological event in the innermost area of the inner retinal layer for distant transmission through the optic nerve to the lateral geniculate area of the brain.

As the output of each photodiode will be automatically amplitude modulated corresponding to the intensity of the incident light, the resulting stimulation and signal current production of the overlying photoreceptor or bipolar cell layer will also be amplitude modulated thereby duplicating the normal amplitude-modulated character of these cells. Stimulating inner retina 56 at the above indicated location will also allow the normal function of the horizontal cell on-off receptor fields thereby allowing contrast appreciation.

Although recognizable color information output may not occur from the stimulated cells, significant formed vision output should develop serving as input for the amacrine and ganglion cell layers which will modify the signal into a frequency modulated signal for transmission to the lateral geniculate area of the brain.

While several embodiments of this invention are described, others will be apparent to those of ordinary skill in the art. Such other embodiments are to be included within the scope of the present invention, unless the claims that follow expressly state otherwise.

I claim:

1. An artificial retina device, comprising: a plurality of discrete photodiodes disposed on one surface of a substrate, said photodiodes each including an active electrode layer overlaying a photosensitive layer, each photodiode being connected to an electrical ground, said photodiodes having electrical outputs that correspond to the amplitude of the light incident on said device, whereby said device can be implanted in the eye intermediate the inner retinal layer and the retinal pigment epithelium of outer layer of the retina, so that each of said photodiodes will stimulate directly individual or small groups of cells in the inner retinal layer corresponding to the light incident on said device.

2. The artificial retina device of claim 1, wherein said device is from 3 mm to 20 mm in its maximum width, and from 0.005 mm to 2 mm between said two surfaces.

3. The artificial retina device of claim 1 that further includes a grasping member.

4. The artificial retina device of claim 1 further including a plurality of openings between said two surfaces.

5. The artificial retina device of claim 1 wherein one or both surfaces are curved.

6. The retinal implant device of claim 1, wherein said first surface includes a plurality of protuberances that extend therefrom.

7. The retinal implant device of claim 1, wherein said first surface is flat.

8. The retinal implant device of claim 1 wherein said photosensitive layer comprises a P-doped layer, and said device further includes an intrinsic layer and a N-doped layer, said intrinsic layer being disposed between said P-doped layer and said N-doped layer.

9. The retinal implant device of claim 1 wherein said photosensitive layer comprises a N-doped layer and said device further includes an intrinsic layer and a P-doped layer, said intrinsic layer being disposed between said N-doped layer and said P-doped layer.

10. The retinal implant device of claim 8 wherein said active electrode is formed from polysilicon.

11. The retinal implant device of claim 9 wherein said active electrode is formed from polysilicon.

12. A surgical procedure for implanting a device of claim 1, comprising
    making a horizontal incision temporal to the macula, parallel to and through the nerve fiber layer;
    opening the potential space within the retina by irrigating with balanced salt solution;
    inserting said device into said space intermediate the inner retinal layer and the retinal pigment epithelium of outer layer of the retina with said photodiodes facing light incident into said eye;
    and closing said incision and space.

13. The surgical procedure of claim 12 wherein a plurality of burns are made around the periphery of said device to secure the device in position.

14. A method for producing artificial vision, comprising:
    making an incision through the sclera posterior to the ora serata, through the choroidal vasculature, the outer retinal layer and into the potential space between the inner and outer retinal layer; and
    inserting a device of claim 1 into said space whereby it is positioned in the macula area of the posterior pole of the eye.

15. A method for producing artificial vision, comprising: implanting a device of claim 1 into the potential space of the retina between the retinal pigment epithelium and the inner retinal layer with the active electrode facing light incident the eye, whereby said device intercepts light after its passage through the nerve fiber layer and inner retinal layers of the eye, and produces discrete stimulation from inside the retina of bipolar cells, horizontal cells, amacrine cells and ganglion cells.

* * * * *